(12) United States Patent
Bae et al.

(10) Patent No.: US 7,678,261 B2
(45) Date of Patent: Mar. 16, 2010

(54) APPARATUS AND METHOD FOR MEASURING REACTION RESULT OF SAMPLES ON BIOSENSOR

(75) Inventors: Byung Woo Bae, Anyang-Si (KR); Heon-Kwon Lee, Uiwang-Si (KR); Sung Dong Lee, Seoul (KR); Won Dong Kim, Seoul (KR); Jung Shik Song, Seoul (KR); Jin-A Yoo, Seoul (KR)

(73) Assignee: Infopia Co., Ltd., Anyang-Si, Kyunggi-Do (KR)

( * ) Notice: Subject to any disclaimer, the term of this patent is extended or adjusted under 35 U.S.C. 154(b) by 890 days.

(21) Appl. No.: 10/528,187

(22) PCT Filed: Oct. 4, 2002

(86) PCT No.: PCT/KR02/01853

§ 371 (c)(1),
(2), (4) Date: Mar. 17, 2005

(87) PCT Pub. No.: WO2004/029605

PCT Pub. Date: Apr. 8, 2004

(65) Prior Publication Data

US 2006/0163086 A1    Jul. 27, 2006

(30) Foreign Application Priority Data

Sep. 30, 2002    (KR) .................. 10-2002-0059612

(51) Int. Cl.
*G01N 33/50* (2006.01)
*G01N 27/327* (2006.01)
*C12Q 1/54* (2006.01)
*C12Q 1/26* (2006.01)

(52) U.S. Cl. .............. 205/777.5; 204/403.01; 204/403.11

(58) Field of Classification Search ............. None
See application file for complete search history.

(56) References Cited

U.S. PATENT DOCUMENTS

| 4,223,549 A | 9/1980 | Kitzinger |
| 5,000,180 A | 3/1991 | Kuypers et al. |

(Continued)

FOREIGN PATENT DOCUMENTS

| DE | 4013593 | 10/1991 |
| GB | 2351153 A | 12/2000 |

(Continued)

OTHER PUBLICATIONS

English Language abstract of DE 40 13 593.
English Language abstract of JP 11-248668.

(Continued)

*Primary Examiner*—Nam X Nguyen
*Assistant Examiner*—Kourtney R Salzman
(74) *Attorney, Agent, or Firm*—Greenblum & Bernstein P.L.C.

(57) ABSTRACT

Disclosed are an apparatus and a method for determining whether or not a biosensor comprising two working electrodes and one reference electrode is well manufactured, and for rapidly and accurately quantifying a specific substance contained in a biological sample. The method comprises the steps of: sequentially supplying the respective working electrodes with power supply voltage; sequentially detecting the amounts of current flowing in the respective working electrodes by virtue of the supplied power supply voltage; re-supplying the two working electrodes with power supply voltage after a predetermined time to redetect the amounts of current flowing in the respective working electrodes; reading concentrations corresponding to the amounts of current detected from a memory, and calculating an average value from the read concentrations; and checking whether or not the concentrations read from memory are within a predetermined critical range to display an error message or the calculated average value.

7 Claims, 7 Drawing Sheets

U.S. PATENT DOCUMENTS

| | | | |
|---|---|---|---|
| 5,120,420 A * | 6/1992 | Nankai et al. | 204/403.11 |
| 5,217,595 A | 6/1993 | Smith et al. | |
| 5,264,103 A | 11/1993 | Yoshioka et al. | |
| 5,672,256 A | 9/1997 | Yee | |
| 5,705,045 A | 1/1998 | Park et al. | |
| 5,951,836 A | 9/1999 | McAleer et al. | |
| 6,340,428 B1 * | 1/2002 | Ikeda et al. | 205/777.5 |
| 6,576,117 B1 * | 6/2003 | Iketaki et al. | 205/777.5 |
| 6,616,819 B1 | 9/2003 | Liamos et al. | |
| 6,635,167 B1 * | 10/2003 | Batman et al. | 205/775 |
| 6,645,368 B1 * | 11/2003 | Beaty et al. | 205/792 |
| 6,730,200 B1 | 5/2004 | Stewart et al. | |
| 6,743,635 B2 * | 6/2004 | Neel et al. | 436/95 |
| 2002/0053523 A1 | 5/2002 | Liamos et al. | |
| 2002/0084196 A1 | 7/2002 | Liamos et al. | |

FOREIGN PATENT DOCUMENTS

| | | |
|---|---|---|
| JP | 5-340915 A | 12/1993 |
| JP | 11-248668 | 9/1999 |
| WO | 01/67099 A1 | 9/2001 |

OTHER PUBLICATIONS

English language Abstract of JP 5-340915 A.

Harrington et al., "Multiple Electrode Potentiostat," Review of Scientific Instruments, AIP, Melville, NY, US, vol. 60, No. 10, Oct. 1, 1989, pp. 3323-3328, XP000071728.

* cited by examiner

APPARATUS AND METHOD FOR MEASURING REACTION RESULT OF SAMPLES ON BIOSENSOR

TECHNICAL FIELD

The present invention relates to a biosensor device. More particularly, the present invention relates to an apparatus and a method for determining whether or not a biosensor comprising two working electrodes and one reference electrode is well manufactured, and for rapidly and accurately quantifying a specific substance contained in a biological sample.

BACKGROUND ART

Generally, a biosensor comprises an electrically insulating base plate, an electrode system including a plurality of electrodes and formed on the electrically insulating base plate using a screen printing method, and an enzyme reaction layer including a hydrophilic polymer, oxidoreductase and an electron acceptor and formed on the electrode system. When a sample liquid containing a substrate is dropped on the enzyme reaction layer of the biosensor, the enzyme reaction layer is dissolved to allow the substrate and enzyme to react with each other. At a result, the substrate is oxidized, and then the electron acceptor is reduced. After such an enzyme reaction finishes, the concentration of the substrate in the sample liquid is determined from an oxidation current obtained by electrochemically oxidizing the reduced electron acceptor.

Figure 1:
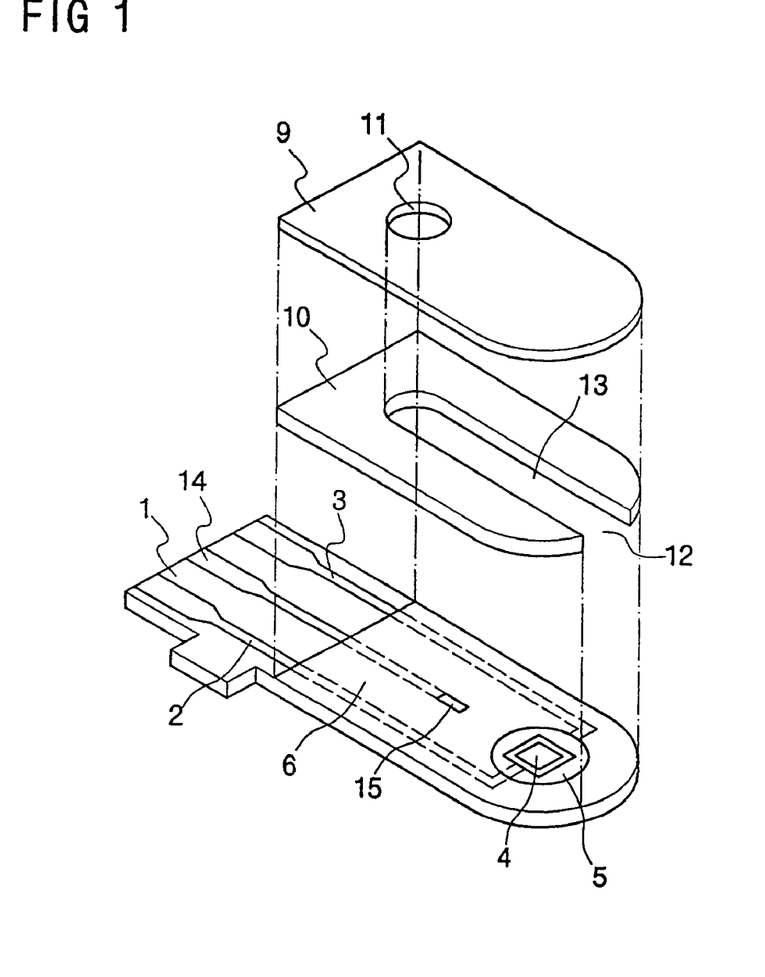
FIG. 1 is an exploded perspective view of a conventional biosensor in which a reaction layer is omitted.
Figure 2:
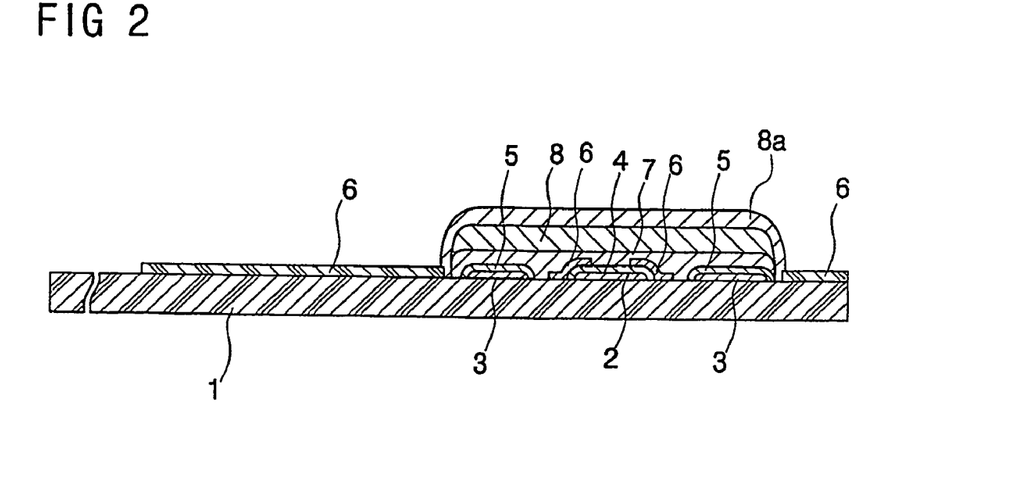
FIG. 2 is a longitudinal sectional view of the biosensor shown in FIG. 1.

As a biosensor for quantifying a specific substance contained in a biological sample using an electrochemical manner, a glucose sensor is known. FIGS. 1 and 2 show a structure of the glucose sensor.

FIG. 1 is an exploded perspective view of a conventional biosensor in which a reaction layer is omitted. FIG. 2 is a longitudinal sectional view of the biosensor shown in FIG. 1.

Referring to FIG. 1, silver paste is screen-printed on an electrically insulating base plate 1 to form leads 2 and 3 on a base plate 1. Conductive carbon paste containing a resin binder is then printed on the base plate 1 to form an operating electrode 4 on the base plate 1. The operating electrode 4 is contacted with the lead 2. Electrically insulating paste is then printed on the base plate 1 to form an insulating layer 6. The insulating layer 6 covers all portions except the operating electrode 4 so that the exposed area of the operating electrode 4 is maintained to be constant. Conductive carbon paste containing the resin binder is printed on the base plate 1 to come into contact with the lead 3 and thus to form a ring-shaped counter electrode 5. Subsequently, on or near an electrode system including the operating electrode and the counter electrode, a reaction layer is formed.

The electrically insulating base plate 1 having the reaction layer and a cover 9 having an air hole 11 are bonded to each other via a spacer 10, along dashed dot lines marked in FIG. 1, to manufacture a biosensor. A slit 13 is formed at the spacer 10 to provide a sample supplying path between the base plate and the cover. Referring to a longitudinal sectional view of the biosensor having the above-mentioned structure, a hydrophilic polymer layer 7 is disposed at the electrically insulating base plate 1 having the electrode system, and a reaction layer 8 including enzymes and electron acceptors and a lecithin layer 8a are disposed on the hydrophilic polymer layer 7 in this order.

When a biological sample is contacted with an introduction port 12 of the biosensor having the above-mentioned structure, the biological sample fills the slit 13 acting as a sample receiving space, and at the same time air in the sample receiving space is vented through an air hole 11 formed at the cover 9.

However, since the air hole 11 is formed at the upper part of the biosensor, the biosensor is disadvantageous in terms of its handling due to measurement errors caused by frequent contact with the air hole 11 when using the biosensor. Considering the fact that the reaction progresses immediately after the sample comes into contact with the reaction layer, it is important to rapidly absorb the sample irrespective of viscosity of the sample. However, in the biosensor having the above-mentioned structure, since the air hole 11 for venting air is arranged at the rear side of a sample introduction passage, rapid absorption of the sample is limited.

Such limited absorption of the sample causes measurement errors in biosensors that initiate the measurement after checking whether or not the sample is completely introduced. The measurement errors are mainly caused by insufficient amount of sample to be introduced, slow absorption of sample and errors generated in the manufacture of a biosensor. In a biosensor including three electrodes, two electrodes must have the same size if possible to minimize the measurement errors. However, since conventional measuring apparatuses cannot detect whether or not the electrodes have the same size and cannot display whether or not the biosensor is properly manufactured, to a user, there exists a danger that the user may erroneously diagnose reaction results of the sample on the biosensor.

DISCLOSURE OF THE INVENTION

Therefore, the present invention has been made in view of the above problems, and it is an object of the present invention to provide an apparatus and a method for measuring reaction results of a sample using a biosensor comprising two working electrodes and one reference electrode. Using the apparatus and method, a reactive substance contained in the sample can be rapidly and accurately quantified.

It is another object of the present invention to provide an apparatus and a method for measuring reaction results of a sample on a biosensor which can display whether or not the biosensor is properly manufactured and errors generated during the use of the biosensor, to a user.

To achieve the above objects, there is provided a method for measuring reaction results of a sample using a biosensor comprising two working electrodes and one reference electrode, comprising the steps of:

sequentially supplying the respective working electrodes with power supply voltage;

sequentially detecting the amounts of current flowing in the respective working electrodes by virtue of the supplied power supply voltage;

re-supplying the two working electrodes with power supply voltage after a predetermined time to redetect the amounts of current flowing in the respective working electrodes;

reading concentrations corresponding to the amounts of current detected from a memory, and calculating an average value from the concentrations; and checking whether or not the concentrations read from the memory are within a predetermined critical range to display an error message or the calculated average value.

The method according to the present invention further comprises the steps of:

determining whether or not an error is generated, by measuring a time interval from when the amount of current flowing in the first working electrode is detected to when the amount of current flowing in the second working electrode is detected and by measuring respective amounts of current detected; and displaying the generated error.

BRIEF DESCRIPTION OF THE DRAWINGS

The above and other objects, features and other advantages of the present invention will be more clearly understood from the following detailed description taken in conjunction with the accompanying drawing, in which.

BEST MODE FOR CARRYING OUT THE INVENTION

Hereinafter, the present invention will be explained in more detail through preferred embodiments, with reference to the accompanying drawings in such a manner that it may easily be carried out by a person having ordinary skill in the art.

Figure 3A:
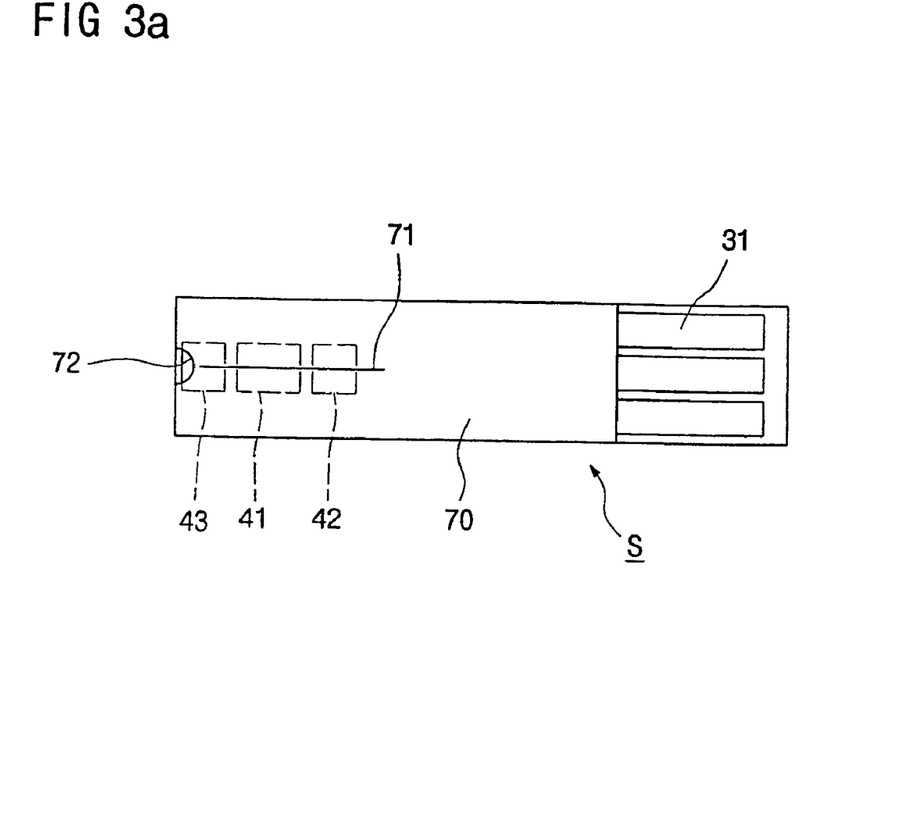
FIGS. 3a and 3b are a top view and a back view of a biosensor according to an embodiment of the present invention, respectively.
Figure 3B:
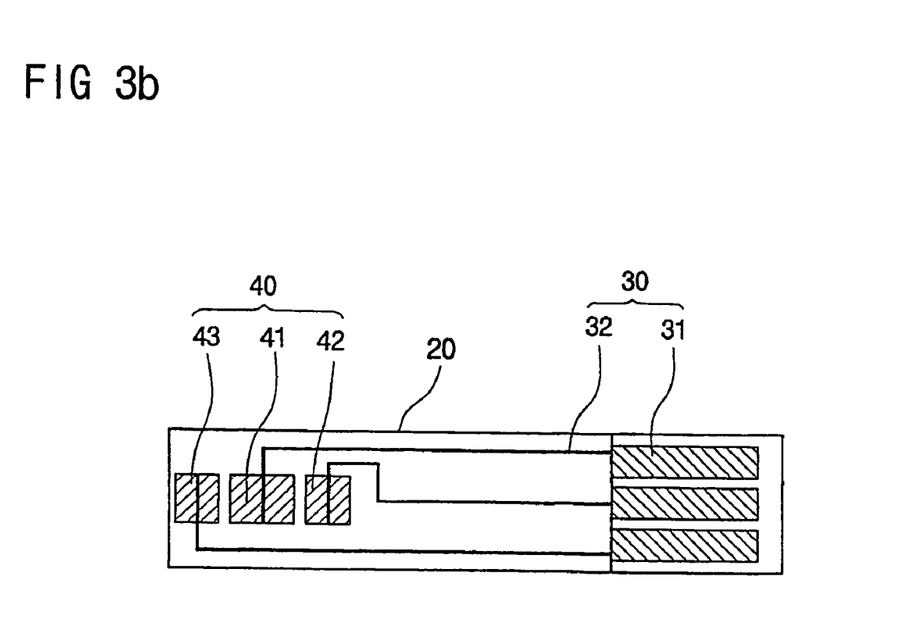
Figure 4:
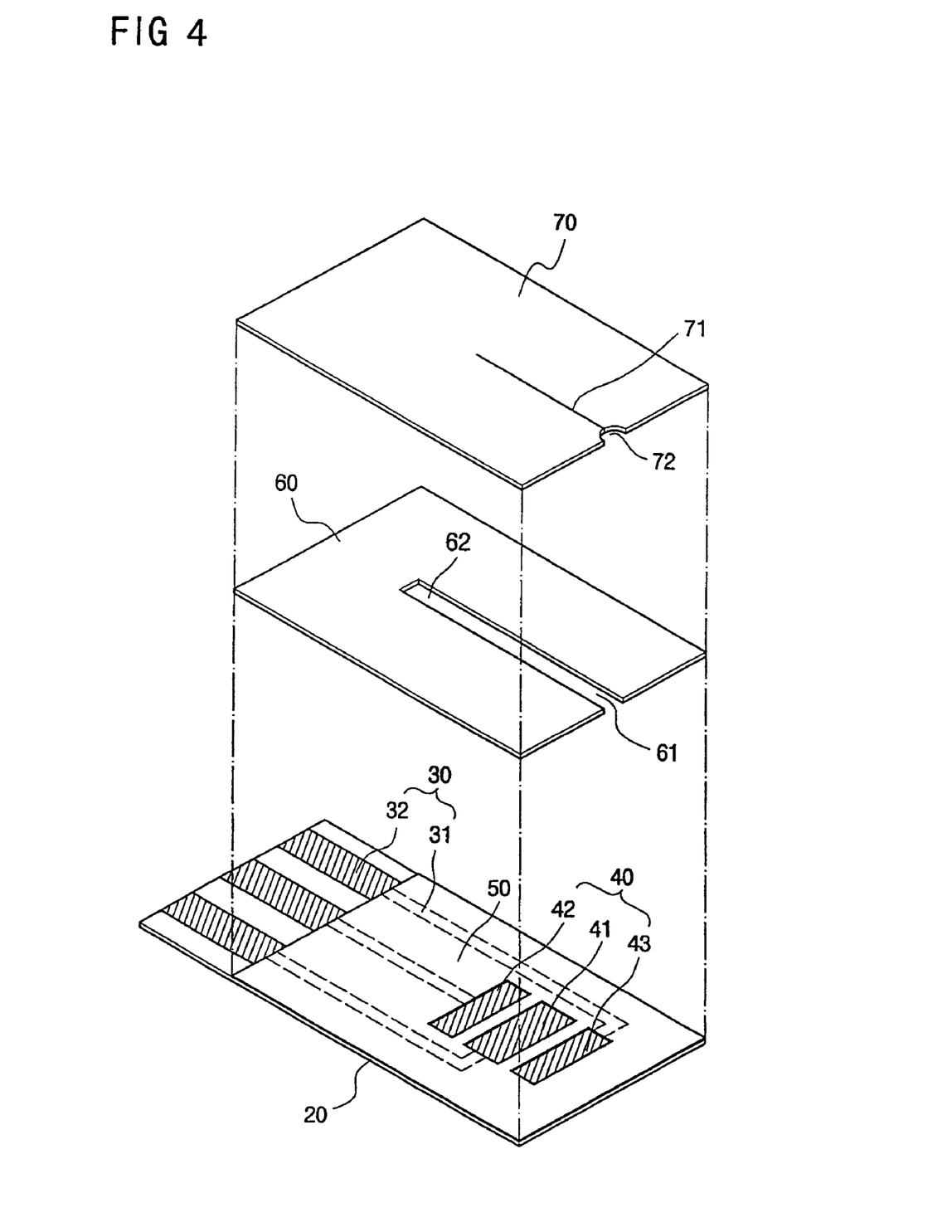
FIG. 4 is an exploded perspective view of the biosensor shown in FIGS. 3a and 3b.
Figure 5:
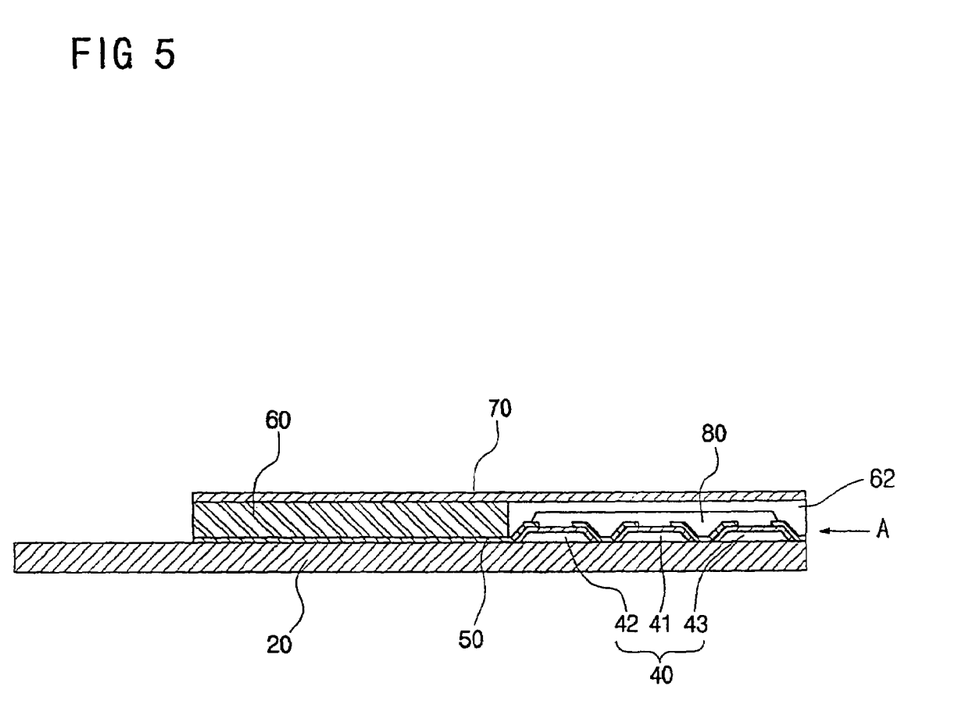
FIG. 5 is a cross-sectional view of the biosensor shown in FIGS. 3a and 3b.

FIGS. 3a and 3b are a top view and a back view of a biosensor, which is combined with an apparatus for measuring reaction results of a sample according to an embodiment of the present invention, respectively. More specifically, FIGS. 3a and 3b are a top view and a back view of the biosensor in the application entitled "biosensor", which was filed with the Korean Intellectual Patent Office (Appln. No. 2002-27971) by the present applicant. FIG. 4 is an exploded perspective view of the biosensor shown in FIGS. 3a and 3b, and FIG. 5 is a cross-sectional view of the biosensor shown in FIGS. 3a and 3b.

Referring to FIG. 3a, the biosensor S combined with the apparatus (so called "biosensor device") for measuring reaction results of a sample according to an embodiment of the present invention is shown. A plurality of lead terminals 31 corresponding to the number of electrodes are formed at one end of an electrically insulating base plate the biosensor S. As shown in FIG. 3b, the lead terminals 31 are connected to electrodes 41, 42 and 43, respectively, formed at the other end of the electrically insulating base plate 20 through respective lead wires 32. As shown in FIG. 3a, a slit 71 is formed at a cover 70 of the biosensor S, and extends from a curved groove 72 formed at one end of the cover 70 toward the electrodes 41, 42 and 43 to at least above the electrodes 41, 42 and 43. The slit 71 acts as an air-vent when a biological sample is introduced by the capillary phenomenon.

The electrically insulating base plate 20 may be made of a non-conductive material such as polyethylene terephthalate, polyvinyl chloride resin, polycarbonate resin, etc. A lead section 30 including the lead wires 32 and the lead terminals 31 may be formed in accordance with a common method such as screen printing. In the electrodes 41, 42 and 43, a reference numeral 41 denotes a reference electrode, and reference numerals 42 and 43 denote working electrodes. These electrodes act to measure the amount of current generated during oxidation and reduction of an electron acceptor included in an enzyme reaction layer 80, which will be discussed below. The reference electrode 41 is arranged between the respective working electrodes 42 and 43. This electrode arrangement makes it possible to measure the amounts of current in the reference electrode 41 and the respective working electrodes 42 and 43. That is, the apparatus according to the embodiment of the present invention detects the amounts of current between the first working electrode 43 and the reference electrode 41, and the second working electrode 42 and the reference electrode 41, determines whether or not there is an error generated in the manufacture of the biosensor and the reaction with a substrate, thereby quantitatively obtaining the concentration of the substrate contained in the biological sample with an increased accuracy.

In accordance with the embodiment of the biosensor according to the present invention, in order to measure the amounts of current in the reference electrode 41 and the respective working electrodes 42 and 43 under the same electrochemical conditions, the respective working electrodes 42 and 43 must have the same electrical resistance and area, and the reference electrode 41 must be spaced at the same distance from the respective working electrodes 42 and 43. In addition, the area of the reference electrode 41 is preferably more than 1.5 times larger than that of the working electrodes 42 and 43. Since the amounts of current generated in the reference electrode 41 and the respective working electrodes 42 and 43 is proportional to the reactive area of the electrodes, the relatively large area of the reference electrode 41 can reduce measurement errors between the reference electrode 41 and the respective working electrodes 42 and 43. The reference electrode 41 and the working electrodes 42 and 43 are collectively referred to as "an electrode system 40". The electrode system 40 can be formed by a screen printing method using a conductive carbon ink.

In order to insulate the electrodes 41, 42 and 43, an insulating material is partially coated on the electrodes 41, 42 and 43 except the upper portions of the electrodes 41, 42 and 43 to form an insulating layer 50, as shown in FIG. 5. As the insulating material, a non-conductive ink for screen printing or an ink for insulation can be used. The enzyme reaction layer 80 is formed on both the exposed portions of the electrodes 41, 42 and 43 and the insulating layer 50. The enzyme reaction layer 80 includes an enzyme reactive with the introduced biological sample, and an electron acceptor.

The enzyme reaction layer 80 must include an enzyme reactive with a substrate to be detected. That is, the enzyme reaction layer 80 can include different enzymes depending on the application of the biosensor. Examples of the enzymes and substrates are shown in Table 1 below. As shown in Table 1, when the biosensor is a glucose sensor, the enzyme reaction layer 80 includes glucose oxidase. When a blood sample as the biological sample is introduced into the enzyme reaction layer 80 of the sensor, glucose in blood % is oxidized by glucose oxidase, after which the glucose oxidase is reduced. Herein, the electron acceptor included in the enzyme reaction layer 80 oxidizes the glucose oxidase and then itself is reduced. The reduced electron acceptor loses its electrons on the surface of the electrode, to which a constant voltage is applied, and then is electrochemically reoxidized. Since the concentration of glucose in the blood sample is proportional to the amount of current generated when the electron acceptor is oxidized, the concentration of glucose in the blood sample can be measured by measuring the amount of current through the lead terminals 32.

TABLE 1

| Substrate | Enzymes |
| --- | --- |
| Glucose | Glucose oxidase |
| Cholesterol | Cholesterol esterase |
| | Cholesterol oxidase |
| | Peroxidase |
| Creatinine | Creatininase |
| | Creatinase |
| | Sarcosine oxidase |
| Lactate | Lactate oxidase |

On the other hand, in accordance with the biosensor S according to the embodiment of the present invention, a spacer 60 having a sample introduction port 61 for forming a sample receiving space is formed on the enzyme reaction layer 80, and is sandwiched between the base plate 20 and the cover 70 as shown in FIG. 4. In order to form the sample receiving space 62 between the cover 70 and the enzyme reaction layer 80 when the cover 70 and the spacer 60 are bonded to each other, the spacer 60 must be higher than the enzyme reaction layer 80 formed on the base plate 20. The spacer 60 can be made of resin. In the embodiment of the present invention, a double-sided tape made of resin was used as the spacer 60.

In accordance with the biosensor S according to the embodiment of the present invention, the cover 70 is bonded to the spacer 60. At this time, in order to vent air existing in the sample receiving space 62 between the spacer 60 and the cover 70, the slit 71 is formed at the cover 70. For stable introduction of the biological sample into above the electrode 42, the slit 71 extends to at least above the electrodes 41, 42 and 43 with a predetermined length.

In the biosensor S as shown in FIG. 5, the spacer 60 is bonded to the upper side of the insulating layer 50. However, the spacer 60 can be directly bonded to the base plate 20 instead of the insulating layer 50.

Hereinafter, structures and operations of the apparatus for measuring reaction results of the sample on the biosensor having the above-mentioned structure will be explained.

Figure 6:
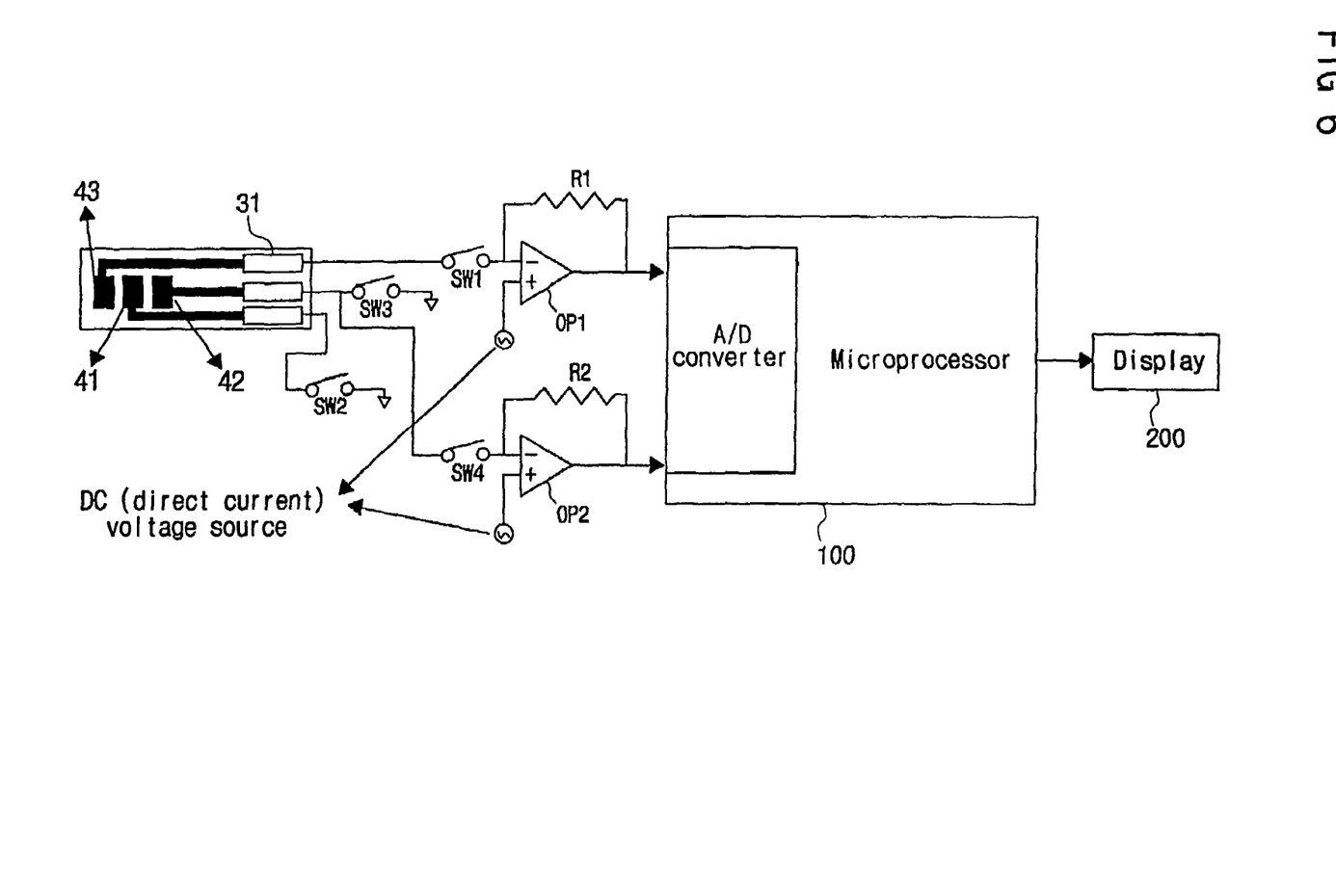
FIG. 6 is a diagram showing a circuit of an apparatus for measuring reaction results of a sample on a biosensor, according to one embodiment of the present invention.
Figure 7:
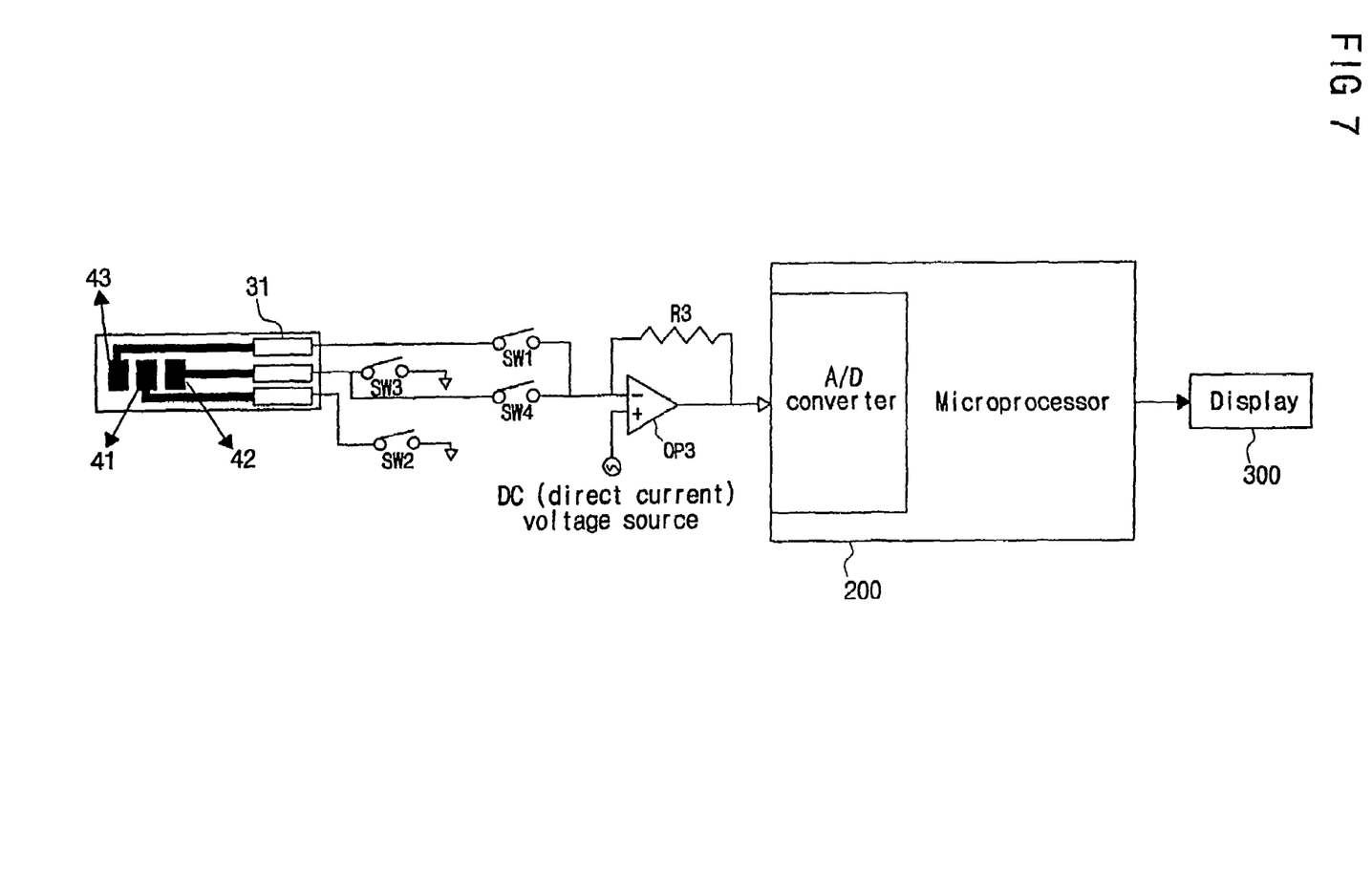
FIG. 7 is a diagram showing a circuit of an apparatus for measuring reaction results of a sample on the biosensor, according to another embodiment of the present invention.

FIG. 6 shows a circuit of the apparatus for measuring reaction results of a sample on the biosensor, according to one embodiment of the present invention, and FIG. 7 shows a circuit of the apparatus for measuring reaction results of a sample on the biosensor, according to another embodiment of the present invention.

Referring to FIG. 6, the apparatus for measuring reaction results of a sample on the biosensor according to the embodiment of the present invention comprises operational amplifiers OP1 and OP2 used as current-voltage converters, switches SW1~SW4, a microprocessor 100 and a display 200.

DC (direct current) voltage source is connected to non-inverting terminals (+) of the respective operational amplifiers OP1 and OP2, and one side of each of a first switch SW1 and a fourth switch SW4 is connected to inverting terminals (−) of the respective operational amplifiers OP1 and OP2, respectively. The other sides of the switches SW1 and SW4 are configured to connect to the lead terminals 31 connected to the first working electrode 43 and the second working electrode 42 of the biosensor, which is combined with the apparatus according to the embodiment of the present invention. The operational amplifiers OP1 and OP2 supply the working electrodes 43 and 42 with power supply voltage, detect the amounts of current flowing in the respective working electrodes by the supplied power supply voltage, and output the amounts of current as voltage values.

On the other hand, the reference electrode 41 of the biosensor combined with the measuring apparatus is connected to the ground through the second switch SW2, and the lead terminal connected to the second working electrode 42 of the biosensor combined with the measuring apparatus is connected to the ground through the third switch SW3. The switches SW1~SW4 are ON/OFF switches under control of the microprocessor 100, which will be described below. The switches SW1~SW4 are used to connect or disconnect current paths of circuit.

The microprocessor 100 controls whole operations of the apparatus for measuring reaction results of a sample on the biosensor, according to the embodiment of the present invention. For example, the microprocessor 100 controls the switches SW1~SW4 to supply two working electrodes 42 and 43 with power supply voltage, and then examines whether or not a sample reaches the electrodes. In addition, the microprocessor 100 controls the switches SW1~SW4 to resupply two working electrodes 42 and 43 with power supply voltage after an incubation time, reads the concentrations corresponding to detected voltage values, calculates an average value from the concentrations, compares the average value with the respective concentrations, and then displays an error message or the average value. Program data for controlling the above process is stored in a memory, which is included in the microprocessor 100. The memory further includes a table in which the concentrations corresponding to the voltage values detected from the working electrodes 42 and 43 are mapped. Further, the microprocessor 100 includes an A/D converter for converting analog voltage values outputted from the operational amplifiers OP1 and OP2 into digital data.

Finally, the display 200 displays data obtained under control of the microprocessor 100. The apparatus according to the embodiment of the present invention further comprises a user interface (not shown) including a plurality of key buttons.

As shown in FIG. 6, the apparatus for measuring reaction results of a sample on the biosensor comprises two operational amplifiers, but the apparatus according to the present invention can comprise only one operational amplifier OP3 as shown in FIG. 7.

In the apparatus shown in FIG. 7, DC voltage source is connected to a non-inverting terminal (+) of an operational amplifier OP3, and one side of each of a first switch SW1 and a fourth switch SW4 is connected to an inverting terminal (−) to connect to the first working electrode 43 and the second working electrode 42 of the biosensor. On the other hand, the reference electrode 41 of the biosensor combined with the measuring apparatus is connected to the ground through a second switch SW2, and the lead terminal connected to the second working of the biosensor combined with the measuring apparatus is connected to the ground through a third switch SW3. The switches SW1~SW4 are turned ON/OFF under control of the microprocessor 100.

Figure 8:
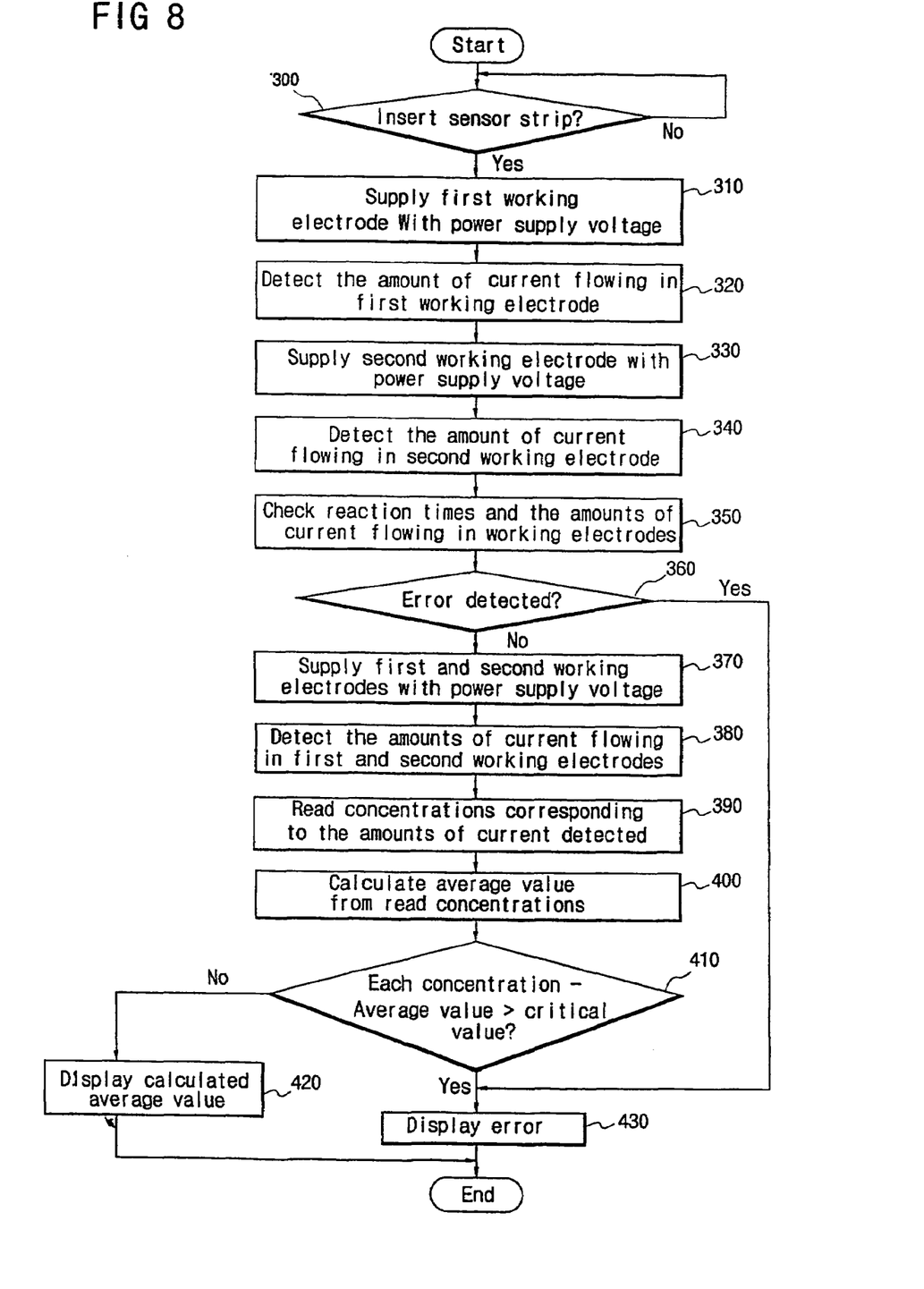
FIG. 8 is a flowchart showing a method for measuring reaction results of a sample on a biosensor, according to the embodiment of the present invention.

Hereinafter, operations of the measuring apparatus shown in FIG. 6 will be explained in more detail, with reference to FIG. 8. FIG. 8 is a flowchart showing a method for measuring reaction results of a sample on the biosensor, according to the embodiment of the present invention.

Referring to FIG. 8, first, a user contacts a sample liquid such as blood to the curved groove 72 of the biosensor, and then inserts the sensor into an insertion groove of the measuring apparatus. At this step, the microprocessor 100 examines whether or not the biosensor is properly inserted (step 300). This examination is performed by the fact that when the biosensor is inserted into the measuring apparatus to short a switch located in the insertion path, input power source voltage drops to 0V. In addition, the examination can be performed based on grounding of recognition electrode, like common measuring apparatuses.

As such, when the biosensor is inserted into the measuring apparatus, the microprocessor 100 is converted into a mode for detecting reaction results of a sample, and then supplies the first working electrode with power supply voltage (step 310). For supplying the power supply voltage, the switches 1 and 2 (SW1, SW2) are turned ON, and the switches 3 and 4 (SW3, SW4) are maintained to be OFF.

When the sample reaches the reference electrode through the first working electrode 43 of the biosensor, a current flows between two electrodes 41 and 43 by a reaction in the enzyme reaction layer 80. The current flowing in the first working electrode 43 is converted into a voltage by a resistance R1 connected to an output terminal and the inverting terminal (−) of the operational amplifier OP1. The converted voltage is inputted to the microprocessor 100, and then is preferentially converted into digital data. Accordingly, the microprocessor 100 can detect a voltage value converted into digital data, that is, the amount of current flowing in the first working electrode 43 (step 320). After detecting the amount of current flowing in the first working electrode 43, the microprocessor 100 starts counting a time interval until a current flowing in the second working electrode 42 is detected. The counted time interval is used to determine whether or not the sample is securely introduced.

After the microprocessor 100 detects the amount of current flowing in the first working electrode 43 and starts the time-counting, it supplies the second working electrode 42 with power supply voltage (step 330). For supplying the second working electrode with the power supply voltage, the switches 2 and 4 (SW2, SW4) are turned ON, and the switches 1 and 3 (SW1, SW3) are turned OFF. This supply of the power supply voltage to the second working electrode 42 is to examine whether or not the sample securely reaches the second working electrode 42. Accordingly, to examine whether or not the sample reaches the second working electrode 42, the switches 2 and 4 (SW2, SW4) can be turned OFF, and the switches 1 and 3 (SW1, SW3) can be turned ON. At this step, the second working electrode 42 acts as a reference electrode.

As described above, after supplying the second working electrode 42 with power supply voltage, the microprocessor 100 detects the amount of current flowing in the second working electrode (step 340). When the amount of current flowing in the second working electrode 42 is detected, a counted time value (that is, reaction time in the respective working electrodes 43 and 42) from when the amount of current flowing in the first working electrode 43 is detected to when the amount of current flowing in the second working electrode 42 is detected is obtained. It is then checked if the value is within a predetermined critical range (step 350). Through the checking, the microprocessor 100 can determine whether or not an error is generated during introduction of the sample (step 360). In addition, the microprocessor 100 checks the amounts of current flowing in the working electrodes 43 and 42 (step 350) to determine whether or not the electrodes are well manufactured. For example, if one of the electrodes is over-sized in its area, difference between the amounts of current flowing in the over-sized electrode and the other electrode will become large. Accordingly, the microprocessor 100 can determine whether or not the biosensor is well manufactured simply by comparing the amounts of current flowing in the working electrodes 43 and 42.

If it is determined that an error is generated during introduction of the sample or manufacture of the working electrodes by checking the reaction time and the amounts of current detected in the respective working electrodes 43 and 42, the microprocessor 100 displays the error (step 430). On the contrary, if the sample introduction and manufacture of the working electrodes are determined to be normal (step 360), the microprocessor 100 maintains all switches 1, 2, 3 and 4 to be OFF for a predetermined incubation time. The incubation time is provided to ensure that reaction in the electrodes is homogeneous. However, the incubation time is not necessarily required. In addition, for rapid measurement, switches 1, 2 and 4 can be turned ON and switch 3 can be turned OFF.

After a predetermined time (or the incubation time), the microprocessor 100 supplies the first working electrode 43 and the second working electrode 42 with power supply voltage, sequentially (step 370). The microprocessor 100 then detects the amounts of current flowing in the first working electrode 43 and the reference electrode 41, and the second working electrode 42 and the reference electrode 41, respectively (step 380). Switch control is required to supply the power supply voltage to the respective working electrodes and to detect the amounts of current in the respective working electrodes.

After the microprocessor 100 detects the amounts of current flowing in the first working electrode 43 and the second working electrode 42 upon the switches 1, 2 and 4 being turned ON, it reads the concentrations corresponding to the amounts of current detected in an internal memory (step 390). Strictly speaking, the amounts of current detected indicate voltage values outputted from the operational amplifiers OP1 and OP2. Thereafter, the microprocessor 100 calculates an average value from the concentrations read in the internal memory (step 400).

If the calculated average value is out of a predetermined critical range by more than 20% (step 410), there is a possibility that an error may occur during manufacturing the working electrodes or the substrate. At this time, the microprocessor 100 displays the error (step 430). However, if the difference between the concentrations and the calculated average value is within the critical range, the microprocessor 100 displays the calculated average value (step 420).

Accordingly, the apparatus according to the present is invention can check whether or not a sample securely reaches two working electrodes, and determine whether or not the biosensor is properly manufactured by detecting the amounts of current flowing in the working electrodes before or after an incubation time.

INDUSTRIAL APPLICABILITY

As described above, according to the present invention, measurement errors by the biosensor can be minimized by detecting the amounts of current flowing in the two electrodes and one reference electrode, and averaging the measured values. In addition, the apparatus according to the present invention can check whether or not a sample securely reaches two working electrodes by detecting the amounts of current flowing in the working electrodes, and display an error generated during the use of the biosensor to a user. Furthermore, since the apparatus according to the present invention can check whether or not the biosensor is properly manufactured by detecting the amounts of current flowing in the working electrodes, it can prevent the user from erroneously diagnosing reaction results of the sample on the biosensor due to an incorrectly manufactured biosensor.

While the present invention has been described with regard to preferred embodiments thereof, the description is for illustrative purposes only and is not to be construed as limiting the scope of the invention. It is understood that various modifications and changes may be made from the description by those skilled in the art. For example, although an application entitled "biosensor" which was filed by the present applicant is exemplified in the detailed description, any biosensor including two working electrodes and one reference electrode can be combined with the apparatus according to the present invention to measure reaction results of a sample on the biosensor. Accordingly, the true scope of the invention is defined only by the appended claims.

The invention claimed is:

1. A method for measuring reaction results of a sample using a biosensor having two working electrodes and one reference electrode, comprising:
   sequentially supplying respective working electrodes with a power supply voltage and measuring a time interval from when an amount of current flowing in a first working electrode begins to be detected until a time when an amount of current flowing in a second working electrode begins to be detected;
   displaying an error message when the measured time interval exceeds a predetermined critical range;
   sequentially re-supplying the respective first and second working electrodes with the power supply voltage when the measured time interval is within the predetermined critical range, and re-detecting the amounts of current flowing in the respective first and second working electrodes;
   reading concentrations corresponding to the amount of current from a memory and calculating an average value from the read concentrations; and
   checking whether a difference between each of the concentrations read from the memory and an average value exceeds a predetermined critical value to display one of an error message and the calculated average value.

2. An apparatus for measuring reaction results of a sample using a biosensor having two working electrodes and one reference electrode, comprising:
   at least one operational amplifier that detects an amount of current flowing in respective working electrodes and outputs an amount of current as voltage values, wherein a non-inverting terminal of the operational amplifier is connected to a voltage source and an inverting terminal of the operational amplifier is connected to a first switch;
   a second switch that selectively grounds the reference electrode of the biosensor;
   a third switch that selectively grounds one of the two working electrodes of the biosensor;
   a display that displays at least one of reaction results of the sample and an error message; and
   a microprocessor configured to control at least one of the first, the second and the third switch to supply the two working electrodes with a power supply voltage, to detect the current in the first and second working electrodes, to examine whether the sample reaches the two working electrodes, to measure a time interval from when an amount of current flowing in a first working electrode begins to be detected until an amount of current flowing in a second working electrode begins to be detected, to display an error message when the measured time interval exceeds a predetermined critical period, to resupply the first and second two-working electrodes with the power supply voltage by controlling at least one of the first switch, the second switch and the third switch when the measured time period is within the predetermined critical range, to redetect respective amounts of current flowing in the first working electrode and the second working electrode, to read, concentrations corresponding to detected voltage values, to calculate an average value from the read concentrations, to check whether a difference between each of the read concentrations and the average value exceeds a predetermined critical value, and to display one of an error message when the difference exceeds the predetermined critical value or the calculated average value when the difference is within the-predetermined critical value.

3. The method for measuring reaction results of a sample as set forth in claim 1, further comprising checking whether the sample is properly inserted.

4. The method for measuring reaction results of a sample as set forth in claim 3, further comprising displaying an error message when the sample is not properly inserted.

5. The method for measuring reaction results of a sample as set forth in claim 1, further comprising providing an incubation time before resupplying the two working electrodes with the power supply voltage.

6. The apparatus for measuring reaction results of a sample as set forth in claim 2, further comprising a memory having a table of concentrations corresponding to the voltage values or amount of current detected from the two working electrodes.

7. The method of claim 1, further comprising:
   comparing the amount of current flowing in the first working electrode and the amount of current flowing in the second working electrode and displaying an error message when a difference between the amount of current flowing in the first working electrode and the second working electrode exceeds the predetermined critical range.

* * * * *

UNITED STATES PATENT AND TRADEMARK OFFICE
CERTIFICATE OF CORRECTION

| | | |
|---|---|---|
| PATENT NO. | : 7,678,261 B2 | Page 1 of 1 |
| APPLICATION NO. | : 10/528187 | |
| DATED | : March 16, 2010 | |
| INVENTOR(S) | : Byung-Woo Bae et al. | |

It is certified that error appears in the above-identified patent and that said Letters Patent is hereby corrected as shown below:

At column 10, line 16 (claim 2, line 27) of the printed patent, change "two-working" to --working--.

Signed and Sealed this

Twenty-ninth Day of June, 2010

David J. Kappos
*Director of the United States Patent and Trademark Office*